US012805692B2

(12) United States Patent
Sperry et al.

(10) Patent No.: US 12,805,692 B2
(45) Date of Patent: Nov. 24, 2026

(54) REUSABLE FOOD OR BEVERAGE CONTAINER SANITIZING AND WASHING SYSTEM

(71) Applicant: Sperry Product Innovation, Inc., Bedford, MA (US)

(72) Inventors: Laurence B. Sperry, Newton, MA (US); Brian A. Murch, Needham, MA (US)

(73) Assignee: Sperry Product Innovation, Inc., Bedford, MA (US)

( * ) Notice: Subject to any disclaimer, the term of this patent is extended or adjusted under 35 U.S.C. 154(b) by 149 days.

(21) Appl. No.: 18/545,168

(22) Filed: Dec. 19, 2023

(65) Prior Publication Data

US 2024/0197140 A1 Jun. 20, 2024

Related U.S. Application Data

(60) Provisional application No. 63/433,791, filed on Dec. 20, 2022.

(51) Int. Cl.
*A47L 15/00* (2006.01)
*A47L 15/42* (2006.01)
(Continued)

(52) U.S. Cl.
CPC ....... *A47L 15/0089* (2013.01); *A47L 15/0071* (2013.01); *A47L 15/4223* (2013.01);
(Continued)

(58) Field of Classification Search
None
See application file for complete search history.

(56) References Cited

U.S. PATENT DOCUMENTS 5,606,759 A 3/1997 Yang
7,875,247 B2 1/2011 Clark et al.
(Continued)

FOREIGN PATENT DOCUMENTS

CN 110507263 A 11/2019
JP 2009011878 A 1/2009
(Continued)

OTHER PUBLICATIONS

Non-Final Office Action in U.S. Appl. No. 18/119,399, dated Sep. 18, 2025.
(Continued)

*Primary Examiner* — Kaj K Olsen
*Assistant Examiner* — Pradhuman Parihar
(74) *Attorney, Agent, or Firm* — Morse, Barnes-Brown & Pendleton, P.C.; Sean D. Detweiler, Esq.

(57) ABSTRACT

A sanitizing and washing system encourages the use of reusable food or beverage containers by utilizing a quick and compact system to sanitize and wash the containers prior to reuse. The doors of the pass-through chamber allow the customer to insert an unsanitized and unwashed container on the entry ("dirty") side of the system, and the retail employee to remove the sanitized and washed container from the exit ("clean") side of the system without having to touch any other surface (doors, knobs, handles, etc.) than the container itself. The system utilizes a UV light source to sanitize the exterior surfaces of the container, while a washing nozzle sprays cleaning fluid to wash and remove residue from the interior surfaces.

24 Claims, 11 Drawing Sheets

(51) Int. Cl.
*A47L 15/48* (2006.01)
*A61L 2/10* (2026.01)
*A61L 2/26* (2006.01)
*A61L 103/00* (2026.01)

(52) U.S. Cl.
CPC ....... *A47L 15/4242* (2013.01); *A47L 15/4246* (2013.01); *A47L 15/4251* (2013.01); *A47L 15/4278* (2013.01); *A47L 15/48* (2013.01); *A61L 2/10* (2013.01); *A61L 2/26* (2013.01); *A61L 2103/23* (2026.01); *A61L 2202/11* (2013.01); *A61L 2202/121* (2013.01); *A61L 2202/122* (2013.01); *A61L 2202/17* (2013.01)

(56) References Cited

U.S. PATENT DOCUMENTS

| | | | |
|---|---|---|---|
| 8,747,770 | B2 | 6/2014 | Davis |
| 9,289,523 | B2 | 3/2016 | Lee |
| 10,155,057 | B2 | 12/2018 | Rizzone |
| 11,992,565 | B2 | 5/2024 | Sperry |
| 2010/0012163 | A1 | 1/2010 | Alpert et al. |
| 2012/0223216 | A1 | 9/2012 | Flaherty et al. |
| 2013/0277574 | A1 | 10/2013 | Dayton |
| 2014/0161663 | A1 | 6/2014 | Farren et al. |
| 2017/0057841 | A1 | 3/2017 | Blood et al. |
| 2017/0186110 | A1 | 6/2017 | Carpenter et al. |
| 2017/0273534 | A1 | 9/2017 | Alpert |
| 2018/0110890 | A1 | 4/2018 | Matsui |
| 2018/0361001 | A1 | 12/2018 | Liao et al. |
| 2019/0321504 | A1 | 10/2019 | Dayton |
| 2021/0225104 | A1 | 7/2021 | Gokcebay et al. |
| 2021/0282621 | A1 | 9/2021 | Disch et al. |
| 2021/0298558 | A1* | 9/2021 | Disch .................. A47L 15/4214 |
| 2021/0308301 | A1* | 10/2021 | Sperry ...................... A61L 2/10 |
| 2021/0369076 | A1 | 12/2021 | McGinness et al. |
| 2022/0079413 | A1* | 3/2022 | Longo ................. A47L 15/0065 |
| 2022/0338706 | A1 | 10/2022 | Disch et al. |
| 2023/0263363 | A1 | 8/2023 | Boyer et al. |
| 2023/0364284 | A1 | 11/2023 | Sperry et al. |

FOREIGN PATENT DOCUMENTS

| | | | |
|---|---|---|---|
| KR | 2010-0007016 | U | 7/2010 |
| KR | 2011-0099351 | A | 9/2011 |
| KR | 2013-0006786 | U | 11/2013 |
| KR | 10-1597453 | | 2/2016 |
| KR | 2016-0098685 | A | 8/2016 |
| TW | 201918264 | A | 5/2019 |
| WO | 2015/012592 | A1 | 1/2015 |
| WO | 2015/080768 | A1 | 6/2015 |
| WO | 2016/054150 | A1 | 4/2016 |
| WO | 2018/187681 | A1 | 10/2018 |
| WO | 2024/137680 | A2 | 6/2024 |

OTHER PUBLICATIONS

< https://verilux.com/products/portable-sanitizing-wand>.
<https://www.phonesoap.com/>.
<https://www.pro.phonesoap.com/>.
<https://www.steri-write.com/>.
<https://www.livelarg.com/>.
Non-Final Office Action in U.S. Appl. No. 17/201,666; dated: Aug. 17, 2023.
Final Office Action in U.S. Appl. No. 17/201,666, dated Dec. 14, 2023.
Signify, Pure Protection Against Viruses and Bacteria [online], Jun. 19, 2021, (retrieved on Feb. 25, 2024]. Retrieved from the internet: <URL: https://web.archive.org/web/20210619100436/https://www.signify.com/enus/innovation/uv-c>.
International Search Report in International Application No. PCT/US2023/084911, dated: May 22, 2024.
Notice of Allowance in U.S. Appl. No. 18/119,399, dated: Jan. 31, 2024.

* cited by examiner

REUSABLE FOOD OR BEVERAGE CONTAINER SANITIZING AND WASHING SYSTEM

CROSS-REFERENCE TO RELATED APPLICATION(S)

This application claims priority to, and the benefit of, U.S. Provisional Application 63/433,791, filed Dec. 20, 2022, for all subject matter common to both applications. The disclosure of said provisional application is hereby incorporated by reference in its entirety.

FIELD OF THE INVENTION

The present invention relates a sanitizing and washing system for reusable food or beverage containers. In particular, the present invention relates to a system which uses ultraviolet (UV) light to sanitize the exterior surfaces of a reusable food or beverage container, and a washing system to clean the interior surfaces of the reusable food or beverage container.

BACKGROUND

With the rapid expansion and size of the to-go food or beverage industry, for example by global businesses including national and international coffee and fast-food chain restaurants, the disposal of single-use drinking containers, especially containers made with plastics, has become a serious problem. This issue is becoming more than just an environmental or public relations issue for the businesses as municipalities have begun to impose taxes on the use of single-use drinking containers. Solutions have been proposed and attempted by manufacturing cups with more environmentally-friendly materials, such as more readily recycled or composted materials. However, the required materials and manufacturing methods have not proven cost-effective as a replacement for existing, commonly used single-use drinking containers. It has also been proven to be difficult to emulate existing desired performance and features using alternate materials.

Systems to provide a means of using reusable drinking containers in place of single-use containers for to-go use have also been proposed and attempted. Such systems are typically comprised of a stock of durable reusable containers which require a deposit from the customer to use for their beverage. When the customer returns the drinking container, the deposit is returned to them. Such systems are typically easy for a customer but increase the labor and required equipment for the retailer to handle and wash the used drinking containers before they can be used again. Such increases have made it a challenge for existing retailers to overcome the cost and infrastructure change of implementing the use of such systems.

Coffee shops, cafes, and other retail establishments that serve beverages often allow customers to bring in their own reusable coffee cups or travel mugs. This trend has a positive impact on reducing the total number of single-use or reusable cups used. Unfortunately, proper cleaning and sanitizing of these reusable cups such that they are safe to be handled and filled by the retail employees requires extensive resources. Additionally, the time and effort required to properly clean and sanitize the cups often prevents users from choosing to bring their own reusable containers.

SUMMARY

There is a need for a small countertop proportioned system that quickly sanitizes and washes reusable food or beverage containers while making it convenient for both the customer and the retail employee to use. In order to quickly and efficiently sanitize and wash the reusable food or beverage container, the system uses UV light to sanitize the exterior surfaces of the reusable food or beverage container, and uses a washing system to clean the interior surfaces of the reusable food or beverage container. This combination of systems can efficiently and effectively sanitize the exterior surfaces to eliminate the potential for the customer spreading germs to the retail employee, while also leaving the exterior surfaces dry and ready to handle. The washing system for the interior surfaces uses water and/or cleaning detergents and the like to clean and remove residue from the interior surfaces of the reusable food or beverage container. The interior surfaces may be left wet in order to minimize the time and energy required for the sanitization and washing cycle, or a drying system can be included to substantially dry the interior surfaces prior to use of the reusable food or beverage container.

A reusable food or beverage container sanitizing and washing system includes a housing, a chamber inside the housing, an access door providing access to the chamber, at least one UV light source and at least one washing nozzle disposed within the chamber. The chamber is sized, dimensioned, and configured to envelope a reusable food or beverage container. When the access door is in an open state, it provides access to the chamber and when the access door is in a closed state is blocks access to the chamber. The at least one UV light source is configured to direct UV light at a predetermined intensity level and time duration onto a reusable food or beverage container positioned inside the chamber in such a way as to result in the sanitizing of the exterior surfaces of the reusable food or beverage container. The at least one washing nozzle is configured to spray cleaning fluid to wash the interior surfaces of the reusable food or beverage container. When the access door is in the closed state, a sanitization and washing cycle is initiated using the UV light source and washing nozzle, and when the sanitization and washing cycle is complete, the access door is moved to the open state.

In accordance with aspects of the present invention, a sanitizing and washing system further includes a retrieval door disposed on a different side of the chamber than the access door, the retrieval door providing access to the chamber when the retrieval door is in an open state and blocking access to the chamber when the retrieval door is in a closed state. In some such aspects, the access door is configured to receive an unsanitized and unwashed reusable food or beverage container and the retrieval door is configured to allow retrieval of a sanitized and washed reusable food or beverage container after the sanitization and washing cycle. In further aspects, the sanitizing and washing system includes a conveyor configured to receive an unsanitized and unwashed reusable food or beverage container, move the unsanitized and unwashed reusable food or beverage container into the chamber through the access door, and move a sanitized and washed reusable food or beverage container out of the chamber through the retrieval door. In some such aspects, the motion of the conveyor is used to dry the interior surfaces of the reusable food or beverage container after the washing cycle. In some aspects, the conveyor comprises a conveyor belt.

In accordance with aspects of the present invention, the sanitizing and washing system further includes a container centering device disposed within the chamber. In some such aspects, the centering device comprises at least one mechanical arm.

In accordance with aspects of the present invention, the at least one UV light source comprises an array of UV lights. In some such aspects, an array of UV light is disposed on an interior surface of one or more sides of the chamber.

In accordance with aspects of the present invention, the predetermined intensity level and time duration result in a UV dose of at least 4 mJ/cm2. In other aspects, the predetermined intensity level and time duration result in a UV dose of about 8 mJ/cm2. In still other aspects, the predetermined intensity level and time duration result in a UV dose of at most 24 mJ/cm2. In further aspects, the predetermined intensity level and time duration result in a UV dose of between about 4 mJ/cm2 and 8 mJ/cm2. In still further aspects, the predetermined intensity level and time duration result in a UV dose of between about 4 mJ/cm2 and 24 mJ/cm2.

In accordance with aspects of the present invention, the at least one UV light source is disposed on a container profiler that is configured to conform to a shape of the container to place the at least one UV light source in proximity to an outer surface of the container allowing for effective sanitation at a lower intensity level or time duration. In some aspects, the profiler comprises one or more members having at least one UV light source mounted thereon, the members configured to move toward an outer surface of the container to place the UV light in proximity to the outer surface of the container. In some such aspects, the container profiler comprises a plurality of linear moving members. In other such aspects, the container profiler comprises articulating members. In further aspects, the profiler includes one or more sensors for detecting the shape of the container. In still other aspects, the container profiler is configured to rotate around the container to distribute application of UV light.

In accordance with aspects of the present invention, the at least one washing nozzle is disposed and configured to wash the interior surfaces of the reusable food or beverage container. In some such aspects, the washing nozzle is configured to extend into the interior of the reusable food or beverage container when activated. In some aspects, a stabilizer is configured to keep the reusable food or beverage container in position within the chamber during the sanitization and washing cycle.

In accordance with aspects of the present invention, the sanitizing and washing system further includes a draining base adapted to receive a reusable food or beverage container in a substantially upside-down orientation. In some such aspects, the draining base is configured to rotate for rotating the reusable food or beverage container within the chamber. In still further aspects, the rotating motion of the draining base is used to dry the interior surfaces of the reusable food or beverage container after the washing cycle.

In accordance with aspects of the present invention, a flipping device is included to receive a reusable food or beverage container in a substantially upright position and turn the container over to allow the container to drain during or after the washing cycle.

In accordance with aspects of the present invention, one or more dryers are included to dry the interior surfaces of the reusable food or beverage container at the end of the washing cycle.

In accordance with aspects of the present invention, the housing rotates around the chamber and wherein the access door, connected to the housing, receives unsanitized and unwashed reusable food or beverage container in a first position located on a first side of the chamber and rotates to a second position located on second side of the chamber to provide access to a sanitized and washed reusable food or beverage container. In some aspects, sliding members of the housing rotate around the chamber and wherein the sliding members provide an access door which receives unsanitized and unwashed reusable food or beverage container in a first position located on a first side of the chamber and rotate to a second position located on second side of the chamber to provide access to a sanitized and washed reusable food or beverage container. In some such aspects, the sliding members comprise nesting sliding members. In still further such aspects, the at least one UV light source is disposed on an inner surface of an innermost nesting sliding member.

In accordance with aspects of the present invention, the access door is locked during the sanitization and washing cycle and unlocked after the sanitization and washing cycle is complete. In aspects with a retrieval door, the retrieval door is also locked during the sanitization and washing cycle and unlocked after the sanitization and washing cycle is complete.

In accordance with aspects of the present invention, the access door automatically transitions from a closed state to an open state to receive a reusable food or beverage container. The automated transitioning can be in response to an activation signal provided by a button, switch or sensor. In certain aspects, the automated transitioning is performed in response to an RFID signal provided by an RFID tag provided in or on the reusable food or beverage container. In aspects with a retrieval door, the retrieval door can be similarly automated.

In accordance with aspects of the present invention, the sanitizing and washing system further includes a second chamber inside the housing, a second access door, and at least one UV light source and at least one washing nozzle disposed within the second chamber. The second chamber inside the housing is sized, dimensioned, and configured to envelope a reusable food or beverage container. The second access door provides access to the second chamber when the second access door is in an open state and blocks access to the second chamber when the second access door is in a closed state. The at least one UV light source is configured to direct UV light at a predetermined intensity level and time duration onto a food or beverage container positioned inside the second chamber in such a way as to result in sanitizing of the exterior surfaces of the food or beverage container. The at least one washing nozzle is configured to spray cleaning fluid to wash the interior surfaces of the reusable food or beverage container positioned inside the second chamber. When the second access door is in the closed state, a sanitization and washing cycle is initiated using the UV light source and washing nozzle, and when the sanitization and washing cycle is complete, the second access door is moved to the open state.

In accordance with an embodiment of the present invention, a method for sanitizing and washing a reusable food or beverage container is provided. The method includes providing a sanitizing and washing system as set forth herein, inserting an unsanitized and unwashed reusable food or beverage container into the chamber, initiating a sanitization and washing cycle sanitizing and washing the reusable food or beverage container, and retrieving the now sanitized and washed reusable food or beverage container from the chamber. In accordance with another embodiment, the method includes a dryer to dry the reusable food or beverage container at the end of a washing cycle. In some such embodiments, the dryer is configured to blow, vacuum, or wipe the cleaning fluid to dry the reusable food or beverage container.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
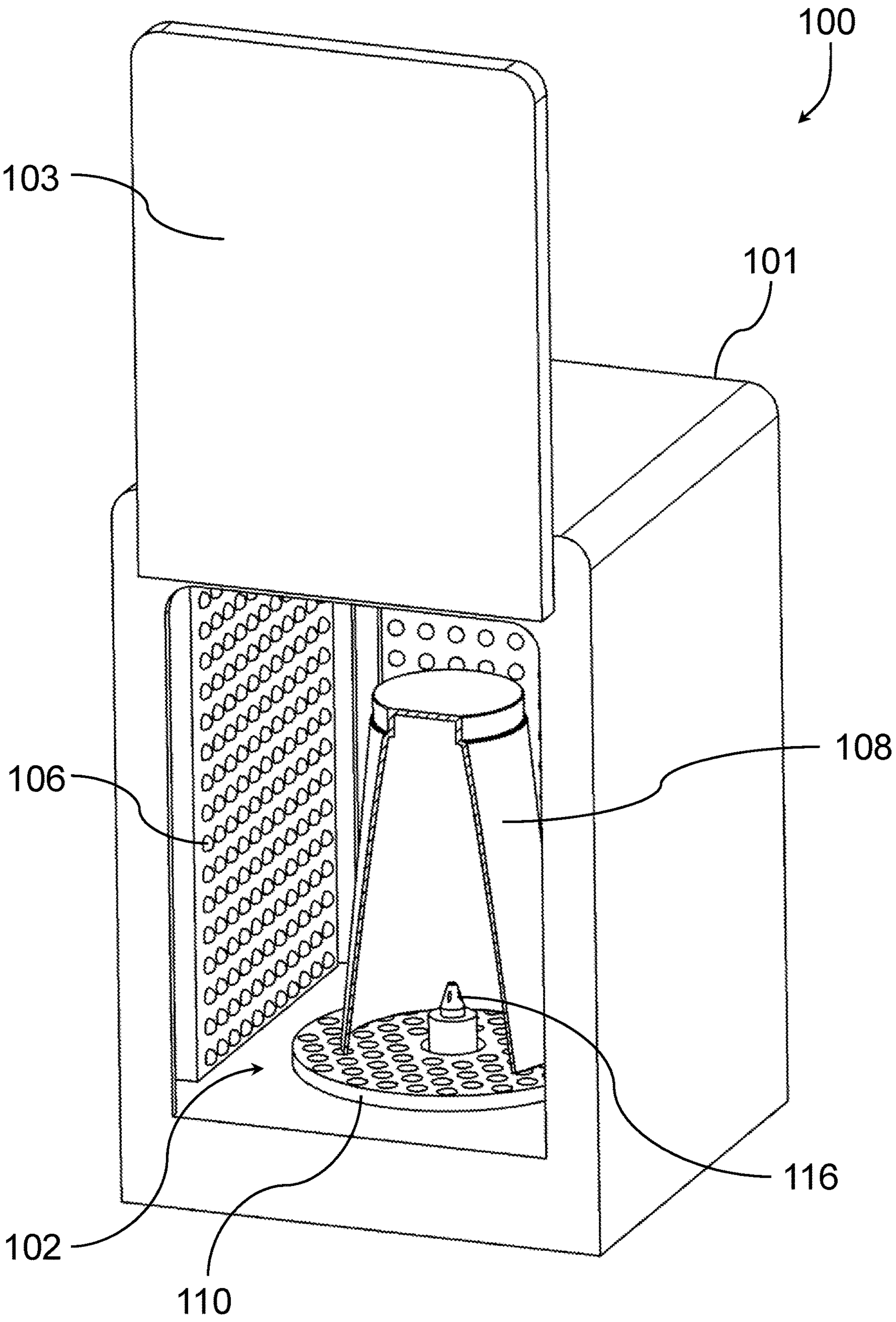
FIG. 1 is an isometric view of a housing of the reusable food or beverage container sanitizing and washing system containing a UV light source and washing nozzle in accordance with embodiments of the present invention.

Illustrative embodiments of the present invention relate to preventing the spread of harmful germs during the process of reusing cups by utilizing a quick and compact sanitizing and washing system. The doors of a pass-through chamber of the system enable the customer to insert a used food or beverage container, such as a reusable food or beverage container, on the entry ("dirty") side of the system, and the retail employee to remove the sanitized and washed food or beverage container from the exit ("clean") side of the system without having to touch any other surface (doors, knobs, handles, etc.) than the food or beverage container itself. The system utilizes UV light sources to quickly sanitize the exterior surfaces of the food or beverage container, and a washing nozzle to spray cleaning fluid to wash the interior surfaces of the container.

FIGS. 1 through 11, wherein like parts are designated by like reference numerals throughout, illustrate an example embodiment or embodiments of a food or beverage container sanitizing and washing system that is sized, dimensioned, and configured as a countertop system or proportional equivalent, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

The sanitizing and washing system 100 as seen in FIG. 1 comprises a housing 101, a chamber 102 inside the housing 101, an access door 103 providing access to the chamber 102, and at least one UV light source 106 and at least one washing nozzle 116 disposed within the chamber 102. The chamber 102 is sized, dimensioned, and configured to envelope a food or beverage container 108 (shown in a cut-away view for clarity) in a substantially upside-down orientation on a draining base 110. When the access door 103 is in an open state as shown, it provides access to the chamber 102 and when the access door 103 is in a closed state it blocks access to the chamber 102. The at least one UV light source 106 is configured to direct UV light at a predetermined intensity level and time duration onto the exterior surfaces of a food or beverage container 108 positioned inside the chamber 102 in such a way as to result in sanitizing of the exterior surfaces of the food or beverage container 108. The at least one washing nozzle 116 is configured to direct a cleaning fluid in such a way as to result in washing of the interior surfaces of the food or beverage container 108. When the access door 103 is in the closed state a sanitization and washing cycle is initiated using the UV light source 106 and washing nozzle 116 and when the sanitization and washing cycle is complete, the access door 103 is moved to the open state.

In certain embodiments, the sanitizing and washing system 100 is sized and dimensioned to fit on a counter or table top. In some such embodiments, the sanitizing and washing system 100 is configured to be placed and operate on a service counter, or similar, at a food or beverage service location. As such, the sanitizing and washing system has similar dimensions as other countertop devices such as toaster ovens or coffee makers. For example, the sanitizing and washing system 100 may be about 12 inches tall by about 8 inches wide, by about 8 inches deep, or equivalent. In certain such deployments, at least one side of the sanitizing and washing system 100 is accessible from a "customer side" of the counter—that is the side of the service counter that a customer interacts with, while another side of the sanitizing and washing system 100 is accessible from the "employee side" of the counter—that is the side of the service counter that a retail employee interacts with. In certain embodiments, this allows the sanitizing and washing system 100 to act as a pass-through for the transfer of a reusable food or beverage container 108 from a customer to an employee without requiring handling of unsanitized containers 108 by the employee. Other sizes, dimensions, and configurations will be apparent to one skilled in the art given the benefit of this disclosure.

The example reusable food or beverage container sanitizing and washing system 100 depicted in the figures uses a beverage container for the description and figures merely for the purposes of teaching how the invention can be specifically implemented. However, those of skill in the art will readily appreciate that other food or beverage containers can be implemented in the system 100 described herein with modification to some of the components for the specific size, shape, and configuration of the containers, such that the present invention is intended to be universally applicable and operable for a variety of different food or beverage container configurations and is not limited to the specific beverage container shown and described. It should also be appreciated that for purposes of efficiency, the figures provided herewith depicting a beverage container and corresponding system are fully applicable to all possible food or beverage containers and corresponding systems. For the avoidance of doubt, references to the container 108 and corresponding system 100 herein are transferable to other food or beverage containers, such as but not limited to, pizza boxes, Asian food takeout containers, donut boxes, pastry boxes, to-go restaurant food containers, carbonated beverage cups, coffee cups, iced coffee cups, tea cups, water bottles, hot chocolate cups, other disposable food or beverage containers, and the like, which are considered to all fall within the scope of the present inventive system.

Figure 2A:
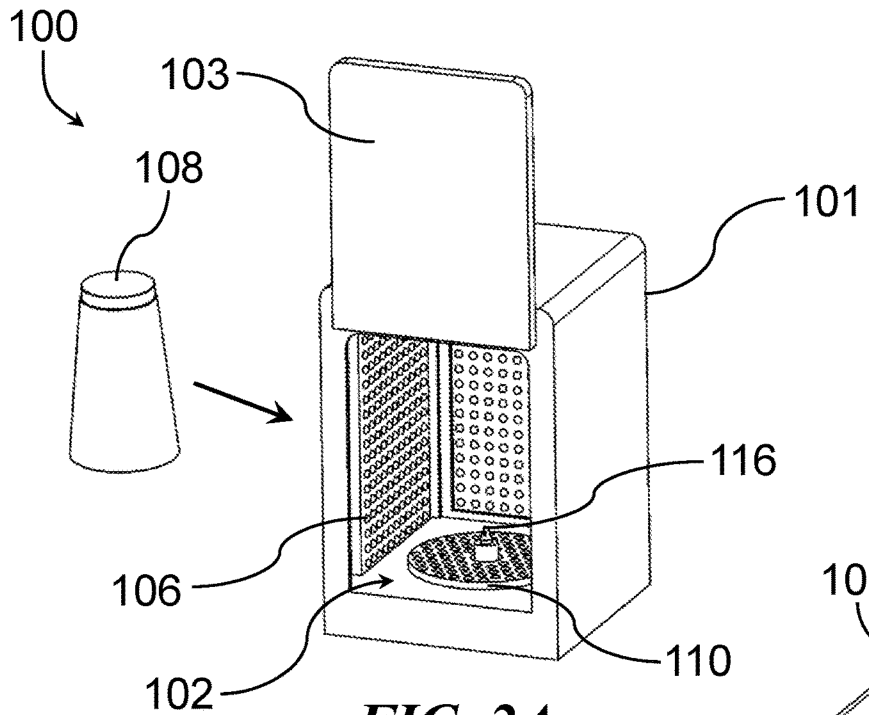
FIGS. 2A, 2B, 2C are isometric views of a housing of the reusable food or beverage container sanitizing and washing system containing a UV light source and washing nozzle in accordance with embodiments of the present invention.
Figure 2B:
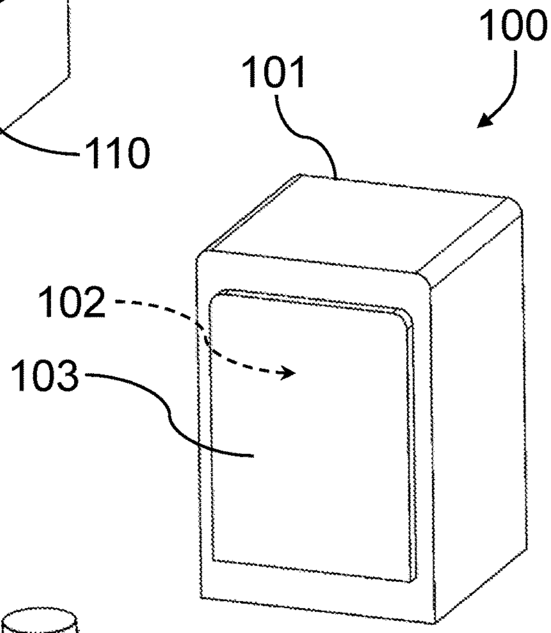
Figure 2C:
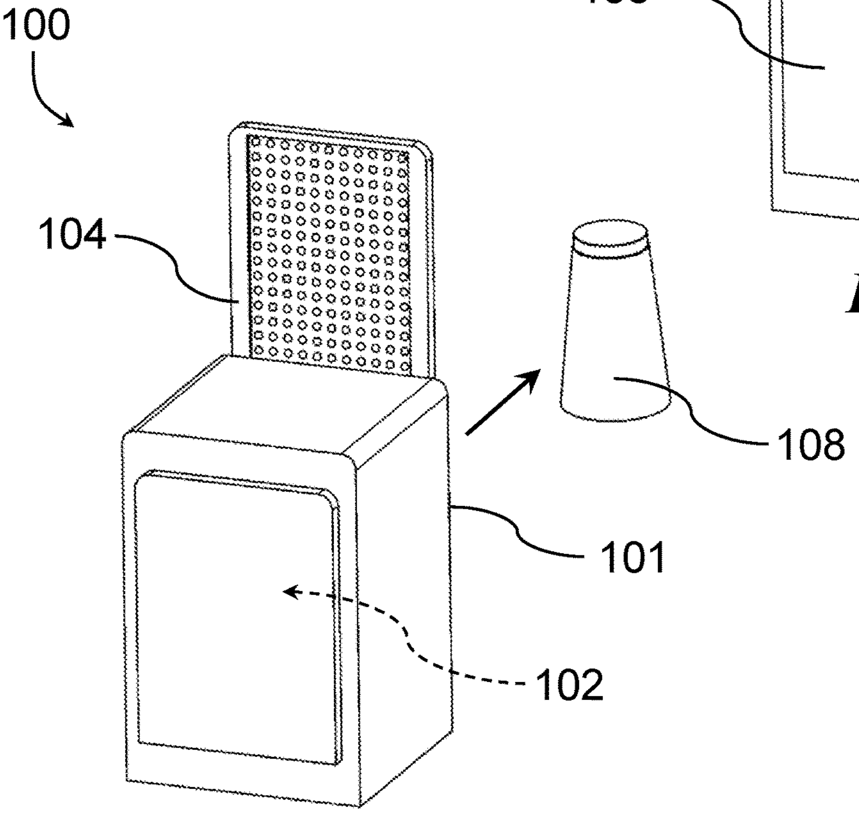

FIGS. 2A-2C depict one embodiment of a system 100 to sanitize the exterior surfaces, using UV-C (or other wavelengths) from at least one UV light source 106, and wash the interior surfaces, using a cleaning fluid sprayed from at least one washing nozzle 116, of a reusable food or beverage container 108 (or any vessel). In this embodiment, the system 100 is comprised of a housing 101 that has access to the chamber 102 from two sides; the entry ("dirty") side having an access door 103 and exit ("clean") side having a retrieval door 104. The system 100 is simple to use for both the customer and retail employee. The term "dirty" as utilized herein refers to a container that has not been sanitized and/or washed or has been utilized or handled since a prior sanitizing and/or washing. The term "clean" as utilized herein refers to a container that has received sanitizing and washing processes utilizing the present invention and is deemed ready for use. In FIG. 2A, the customer places their reusable food or beverage container 108 into the sanitizing and washing system 100 from the "dirty" side via the access door 103 in an open position. In FIG. 2B the access door 103 is moved to a closed state and the reusable food or beverage container 108 is sanitized and washed within the enclosed chamber 102 during a sanitization and washing cycle using at least one UV light source 106 and at least one washing nozzle 116. In this embodiment, the at least one UV light source 106 is an array of UV lights disposed on one or more interior surfaces of the chamber 102. In FIG. 2C, after the sanitization and washing cycle is complete, the retrieval door 104 is moved from a closed state to an open state allowing the retail employee to remove the sanitized and washed container 108 on the "clean" side. In some embodiments of the invention, the food or beverage container 108 is rotated to evenly distribute UV light and cleaning fluid to the surfaces of the food or beverage container 108 to be sanitized and washed. In some embodiments of the invention, the UV light source 106 is rotated to evenly distribute UV light to the exterior surfaces of the food or beverage container 108 to be sanitized. In some embodiments, the washing nozzle 116 is rotated to evenly distribute cleaning fluid to the interior surfaces of the food or beverage container 108 to be washed. In this example, a rotating draining base 110 is provided to rotate the food or beverage container 108 within the chamber 102 providing more thorough exposure to the array of at least one UV light sources 106 disposed on the interior surface of the chamber 102 and more even exposure of the cleaning fluid sprayed from the washing nozzle 116 on to the interior surfaces of the food or beverage container 108. In embodiments of the invention, the draining base 110 can be pervious, porous, perforated, slotted, contain one or more drain holes, or the like to allow the cleaning fluid to drain from the interior of the food or beverage container 108, as would be appreciated by one of skill in the art. In embodiments of the invention, the food or beverage container 108 is placed on to the draining base 110 in a substantially upside-down orientation such that the cleaning fluid will drain out of the food or beverage container by the force of gravity. In other embodiments, the food or beverage container 108 is placed into the chamber 102 in a substantially upright configuration and a flipping device within the chamber turns the food or beverage container 108 over to a substantially upside-down position to allow the cleaning fluid to drain out during or after the washing cycle. In yet another embodiment, the food or beverage container 108 is placed into the chamber 102 in a substantially upright configuration and remains substantially upright for the washing cycle and the cleaning fluid is vacuumed out from the interior of the food or beverage container 108 once the washing cycle is complete.

In some embodiments, the access door 103, as well as the retrieval door 104, to the chamber 102 can be automated to open and close automatically to eliminate the need to touch anything but the food or beverage container 108 itself when using the system 100. In some embodiments, the automatic opening and closing of the door(s) makes it possible to have a single access door 103, such as on the top of the housing 101, for both entry and exit, without the risk of spreading germs. In some such embodiments an identification device, such as an RFID tag, bar-code, QR code, or the like on or embedded within the container 108 is read by a reader of the sanitizing and washing system 100 and is used to unlock the access door 103 or retrieval door 104, automatically open the door 103, 104, or otherwise be used to initiate the sanitization and washing cycle of the device. In still other embodiments, the opening or closing of the doors 103, 104 or the initiation of a sanitization and washing cycle is actuated by a switch, button, motion sensor, or optical sensor. In some such embodiments, the action of placing the food or beverage container 108 into the chamber 102 actuates the switch, button, motion sensor, or optical sensor. Whether manually or automatically closed, the access door 103, as well as the retrieval door 104, can be locked during the sanitization and washing cycle as a safety precaution to prevent inadvertent UV exposure to a user. Conversely, there can be an automatic shut-off of the one or more UV light sources 106 and spray from the one or more washing nozzles 116 if the access door 103 or retrieval door 104 are opened before a sanitization and washing cycle is complete. In an embodiment of the invention, the access door 103 and retrieval door 104 are closed between cycles such that the at least one UV light source 106 and/or at least one washing nozzle 116 are used to sanitize and/or wash the interior surfaces of the chamber 102.

Figure 3A:
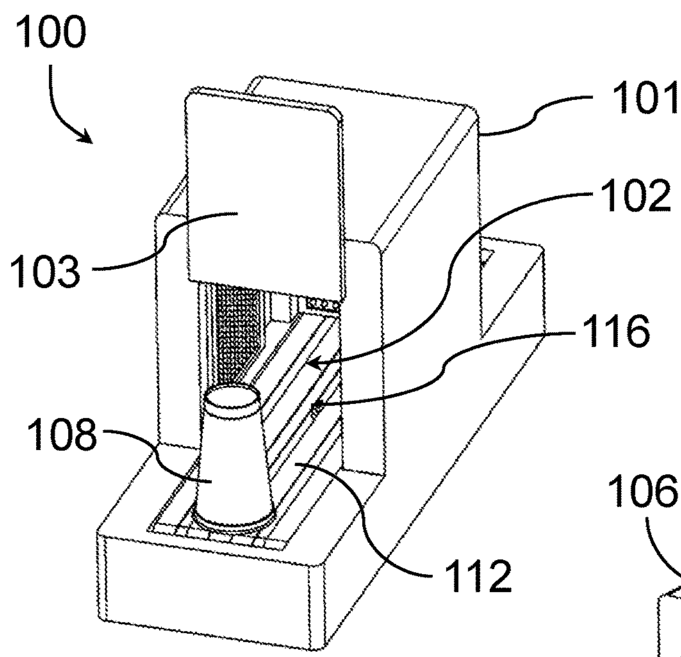
FIGS. 3A, 3B, 3C are isometric views of a housing of the reusable food or beverage container sanitizing and washing system with conveyance containing a UV light source and washing nozzle in accordance with embodiments of the present invention.
Figure 3B:
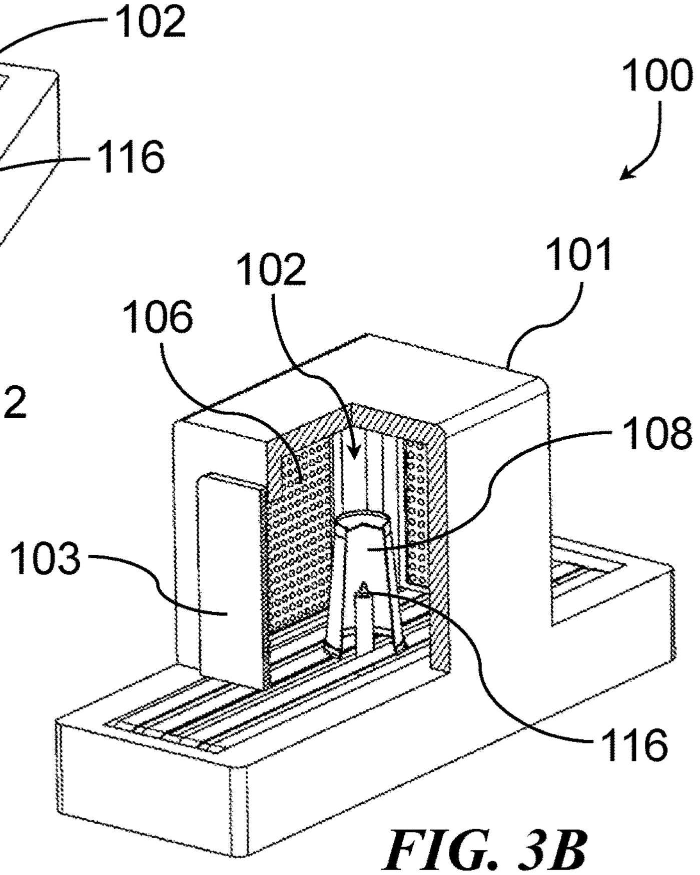
Figure 3C:
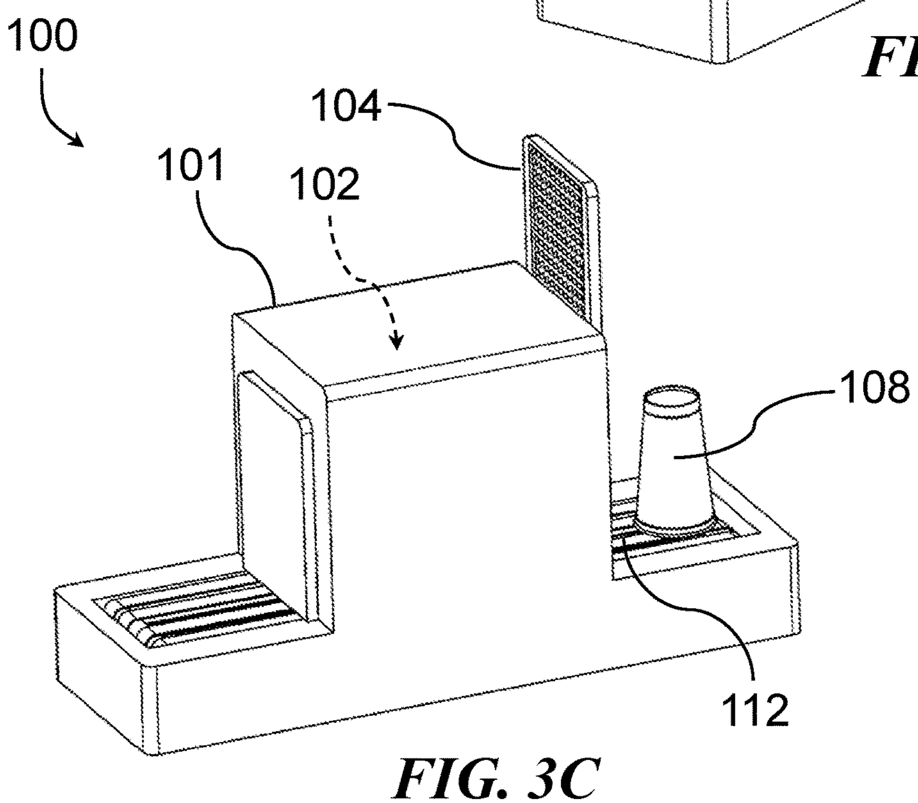

FIGS. 3A-3C depict a system similar to FIGS. 2A-2C with the addition of a conveyor 112 to move the used food or beverage container 108 into the chamber 102 on the "dirty" side and then move the sanitized and washed food or beverage container 108 out of the chamber 102 on the "clean" side. This simplifies the loading and unloading of the system 100, as well as adds the ability to queue additional food or beverage containers 108 to be sanitized and washed. In FIG. 3A, the customer places their food or beverage container 108 onto the conveyor 112, in this case a conveyor belt. In embodiments of the invention, the conveyor 112 can be a series of conveyor belts, a perforated conveyor belt, a segmented conveyor belt, a porous conveyor belt, and the like, to allow the cleaning fluid to drain through the conveyor 112. In other embodiments, the conveyor 112 can be a pushing mechanism to slide the food or beverage container 108 along a draining base 110 (refer to FIG. 1). The conveyor 112 then moves the food or beverage container 108 into the sanitizing and washing system 100 from the "dirty" side via the access door 103 in an open position. In FIG. 3B the access door 103 is moved to a closed state and the food or beverage container 108 (shown in a cut-away view for clarity) is sanitized and washed within the enclosed chamber 102 during a sanitization and washing cycle using at least one UV light source 106 to sanitize the exterior surfaces of the food or beverage container 108 and at least one washing nozzle 116 to wash the interior surfaces of the food or beverage container 108. In this embodiment, the washing nozzle 116 is initially disposed below the top surface of the conveyor 112 (refer to FIG. 3A) as to not interfere with the movement of the food or beverage container 108 along the conveyor 112. Once the food or beverage container 108 is in position to be sanitized and washed, the washing nozzle 116 is configured to rise up into the interior of the food or beverage container 108 when activated (refer to FIG. 3B) to position the washing nozzle 116 in closer proximity to the interior surfaces to be washed. In FIG. 3C, after the sanitization and washing cycle is complete, the retrieval door 104 is moved from a closed state to an open state and the conveyor 112 moves the now sanitized and washed food or beverage container 108 out of the chamber 102 through the retrieval door 104 allowing the retail employee to remove the sanitized and washed food or beverage container 108 from the conveyor 112 on the "clean" side.

One of skill in the art will appreciate that the position of the washing nozzle 116, such as disposed in a fixed position below or substantially flush to the draining base 110 or conveyor 112, fixed in a position extending into the interior of the food or beverage container 108, or movable such that the washing nozzle 116 extends into the interior of the food or beverage container 108 when activated as previously described are applicable to all embodiments of the present invention in keeping with the spirit and scope of the invention. The washing nozzle 116 can be configured to provide the spray of cleaning fluid in a substantially consistent pattern, or can be configured to rotate or oscillate, such as by the force of the spray itself, to provide a dynamically changing spray pattern, as would be appreciated by one of skill in the art.

In embodiments of the invention, the cleaning fluid sprayed from the washing nozzle 116 is water to rinse and remove debris from the interior surfaces. In further embodiments, chemicals are mixed with or used in place of water to more effectively wash and sanitize, such as detergents, rinse aids, sanitizing chemicals, electrolyzed water and the like, as would be appreciated by one of skill in the art. In another embodiment, the cleaning fluid is heated to aid in the removal of debris and sanitization of the interior surfaces of the food or beverage container 108. In another embodiment, the cleaning fluid is heated to the boiling point such that the cleaning fluid is converted to steam to further aid in cleaning and sanitization. In a further embodiment, the steam is pressurized such that it can be heated beyond the boiling point of the cleaning fluid to further enhance the cleaning and sanitization. In another embodiment, mechanical washing means, such as a scrubbing, are used in combination with the cleaning fluid. In additional embodiments, the food or beverage container 108 can be comprised of specialized materials or coatings to enhance washability, such as self-cleaning coatings, hydrophobic coatings, and the like.

Figure 4:
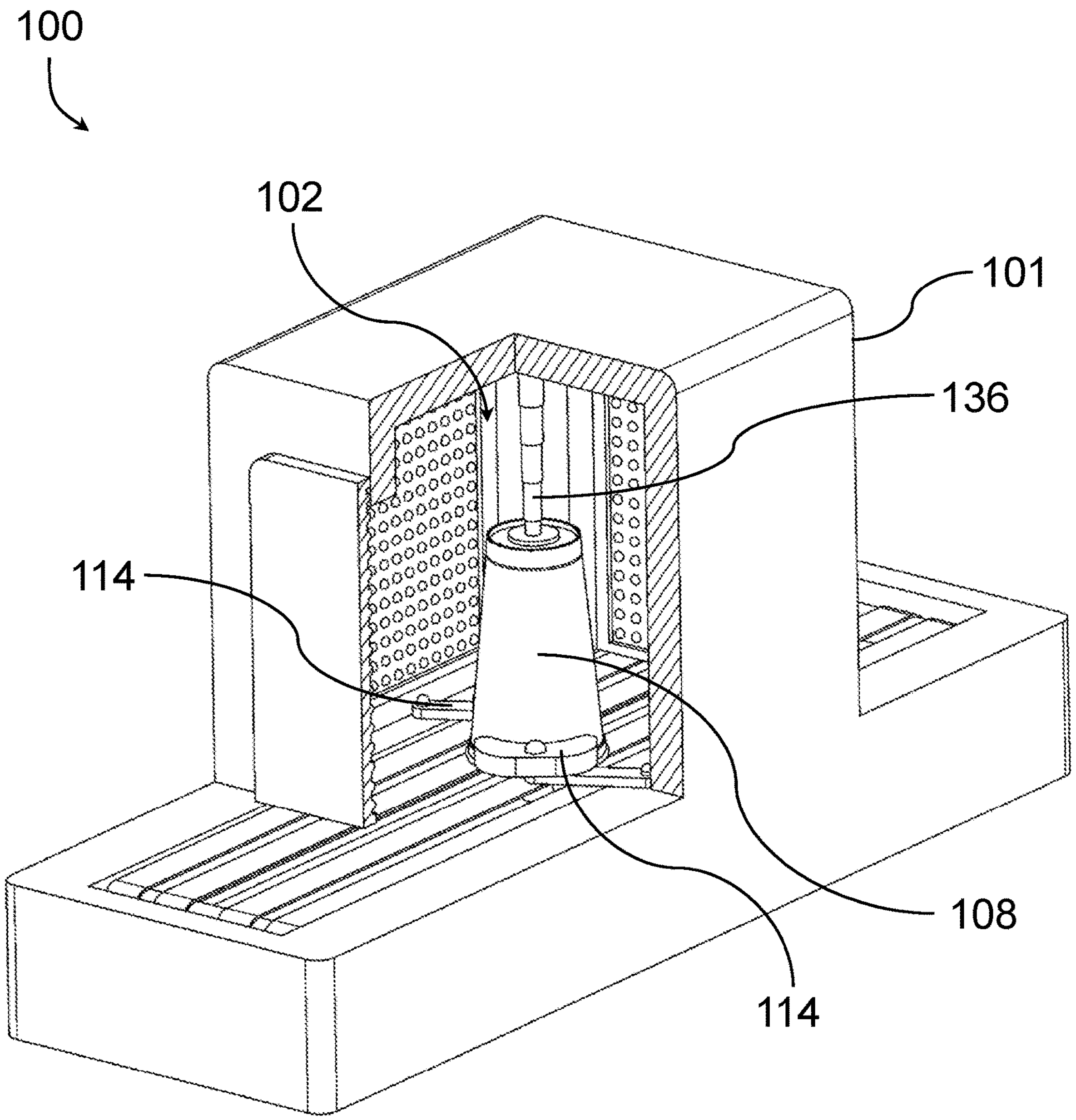
FIG. 4 is an isometric cut-away view of a housing of the reusable food or beverage container sanitizing and washing system with conveyance containing a UV light source, a washing nozzle, centering arms, and a stabilizer in accordance with embodiments of the present invention.

In some embodiments, container centering devices, such as the pivoting centering arms 114, shown in FIG. 4, are utilized to position the food or beverage container 108 in the center of the chamber 102 to ensure the even and expected distribution of UV light on the exterior surfaces and cleaning fluid on the interior surfaces. In some embodiments, a stabilizer 136 is utilized to keep the food or beverage container 108 in the desired position so that the force of the spray of cleaning fluid from the washing nozzle 116 (refer to FIG. 3B) does not move or knock over the food or beverage container 108. In the example embodiment shown in FIG. 4, the stabilizer 136 extends from the top of the chamber 102 to contact the bottom surface of the upside-down food or beverage container 108. In another embodiment, the pivoting centering arms 114 can hold the food or beverage container 108 in position in place of or in addition to the use of the stabilizer 136. In another embodiment, the stabilizer 136 or pivoting centering arms 114 can allow slight movement of the food or beverage container 108 such that the force of the spray from the washing nozzle 116 (refer to FIG. 3B) can jostle, shake, or otherwise move the food or beverage container 108 such that contact points between food or beverage container and components of the system 100, such as the draining base 110, stabilizer 136, and pivoting centering arms 114, change during the sanitization and washing cycle to ensure proper sanitization and washing of all surfaces. In another embodiment, movement of the stabilizer 136 or pivoting centering arms 114 can cause a change in the contact points to ensure proper sanitization and washing of all surfaces as previously described. In another embodiment, the stabilizer 136 or pivoting centering arms 114 are not used while sanitizing and washing and the spray from the washing nozzle 116 (refer to FIG. 3B) is designed to cause slight movement of the food or beverage container 108 to change the contact points between the food or beverage container 108 and the draining base 110 to ensure proper sanitization and washing of all surfaces as previously described.

Although all UV radiation, defined as electromagnetic energy with wavelengths from 100-400 nm, may be used for sanitizing, the UV-C range (100-280 nm) is by far the most effective for sanitizing. In particular, for sanitizing the surfaces of a food or beverage container 108, UV-C in the range of 260-280 nm provides the fastest and most effective sanitization. The amount of UV radiation required to achieve a desired level of sanitation is referred to herein as a Dose (typically units: mJ/cm2). The formula for a Dose can be expressed as the following: Dose=Intensity×Exposure Time. Wherein Intensity is the power per area of surface to be sanitized (typical unit: mW/cm2) and the Exposure Time is the time that the surface is exposed to UV light (typical unit: seconds). Intensity is dependent on the particular UV light being used. For simplicity, the power of the light (in mW) can be used, although in reality, things like lens, coatings, age of light source will affect power of light. But for any UV light (no matter the power or other factors), the intensity is inversely proportional to the square of the distance to the surface (inverse square law function). As such, the closer the light is to the surface, the time required is greatly reduced. For example, at half (½) the original distance, the intensity is quadrupled (4×) so the required time is one quarter (¼) of the original time required. Similarly, if the distance is reduced by half again to a quarter (¼) of the original distance, the intensity is quadrupled again making it sixteen times (16×) more intense, and the exposure time required is one-sixteenth (1/16) of the original time required. As such, the time required to sanitize the food or beverage container 108 using UV light is minimized by moving the at least one UV light source 106 in close proximity to the exterior surface. For the purpose of sanitizing a food or beverage container 108 to prevent the spread of germs in a retail environment, such as a coffee shop or cafe, a UV dose of 8 mJ/cm2 will eradicate more than 99% of common viruses and bacteria, such as SARS-COV-2, influenza A, *E. coli*, RSV, and *salmonella*. In some retail environments, a lower level of sanitization may be used, such as that provided by a UV dose as low as 4 mJ/cm2 to eradicate more than 90% of the viruses and bacteria previously listed. In other environments where there is an increased concern of the transfer of germs, a higher level of sanitization may be used, such as that provided by a UV dose as high or higher than 24 mJ/cm2 to eradicate more than 99.99% of the viruses and bacteria previously listed.

Figure 5A:
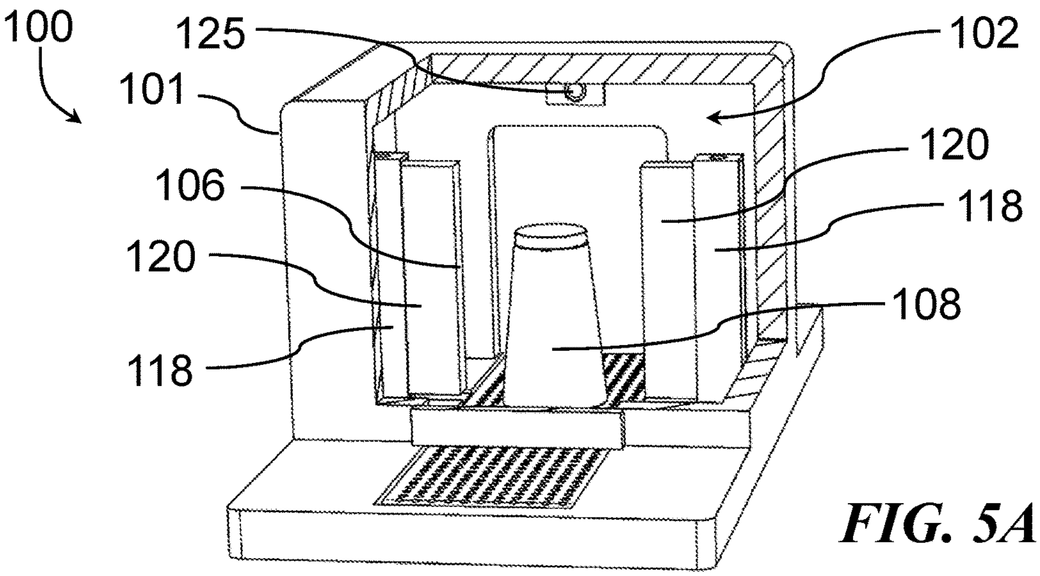
FIGS. 5A, 5B, 5C are isometric cut-away views of a housing of the reusable food or beverage container sanitizing and washing system with conveyance containing a UV light source, a washing nozzle, and a profiler in accordance with embodiments of the present invention.
Figure 5B:
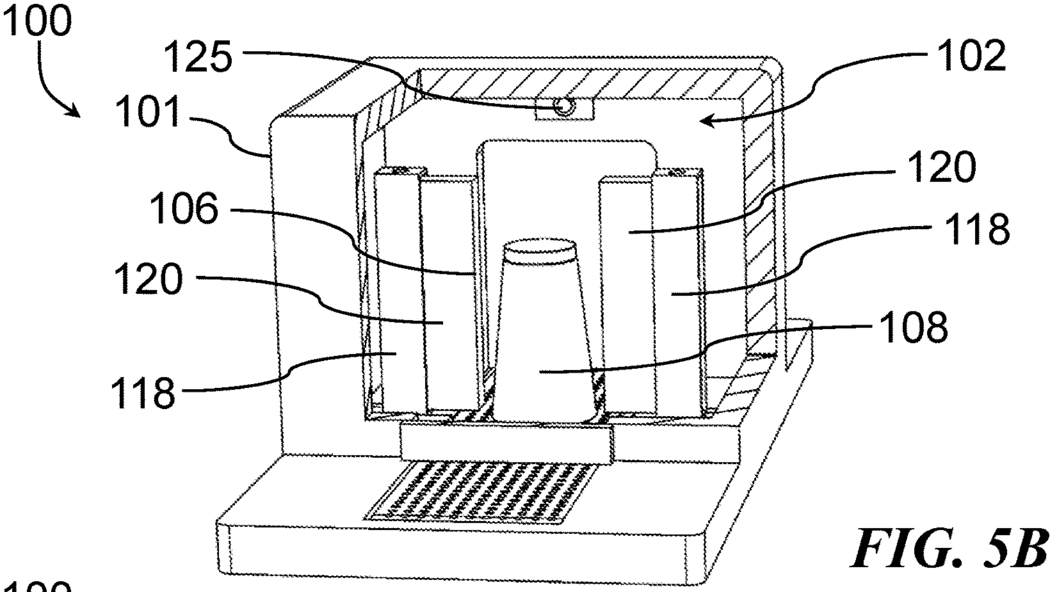
Figure 5C:
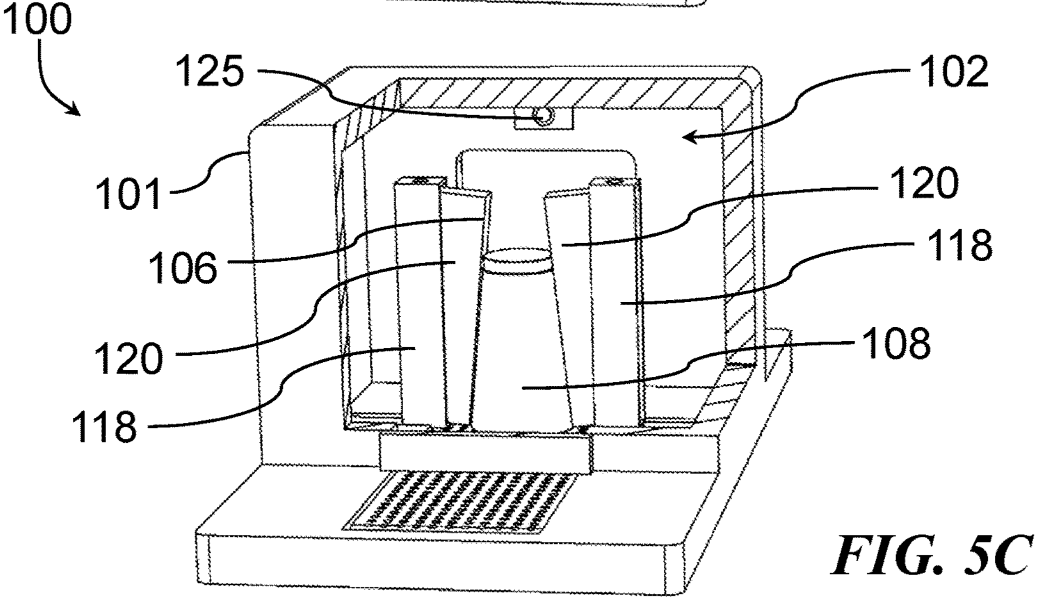

In one embodiment of the current invention shown in FIGS. 5A-5C, the at least one UV light source 106 is disposed on members 120 of a container profiler 118 that is able move the members 120 including the at least one UV light source 106 close to the exterior surface of the food or beverage container 108 and, if required, adjust or otherwise conform to approximately match the tapered shape of commonly used food or beverage containers 108. In FIG. 5A, the profiler 118 is set at a starting position before being positioned to conform to the food or beverage container 108. In the embodiment of FIG. 5B, the profiler 118 has been adjusted to linearly move the members 120 in proximity to the exterior surface of a food or beverage container 108. In certain embodiments, such as seen in FIG. 5C, the members 120 are further capable of moving angularly or otherwise pivoting or tilting to better conform to the profile of the food or beverage container 108.

It should be noted that any of the embodiments described herein can be alternatively embodied in fixed form. Specifically, and for example, looking at the embodiment depicted in FIG. 5C, this embodiment shows the members 120 angularly positioned to match the angle and profile of the food or beverage container 108. In the instance where the food or beverage container 108 will be of a similar shape in every instance of use, the members 120 can be permanently affixed to a shape and/or angle that approximately matches the general shape and profile of a food or beverage container 108 and resemble the device as shown in this figure. In such an embodiment, the members 120 move around the food or beverage container 108 in fixed position, or the food or beverage container 108 can be rotated if the members 120 are fixed, resulting in the full application of UV light to the exterior surfaces of the food or beverage container 108 to achieve the stated desired result. This alternative embodiment of fixed members 120 is anticipated herein for all operable embodiments, and all figures provided herein can be alternatively interpreted to show a fixed profile embodiment.

Figure 6A:
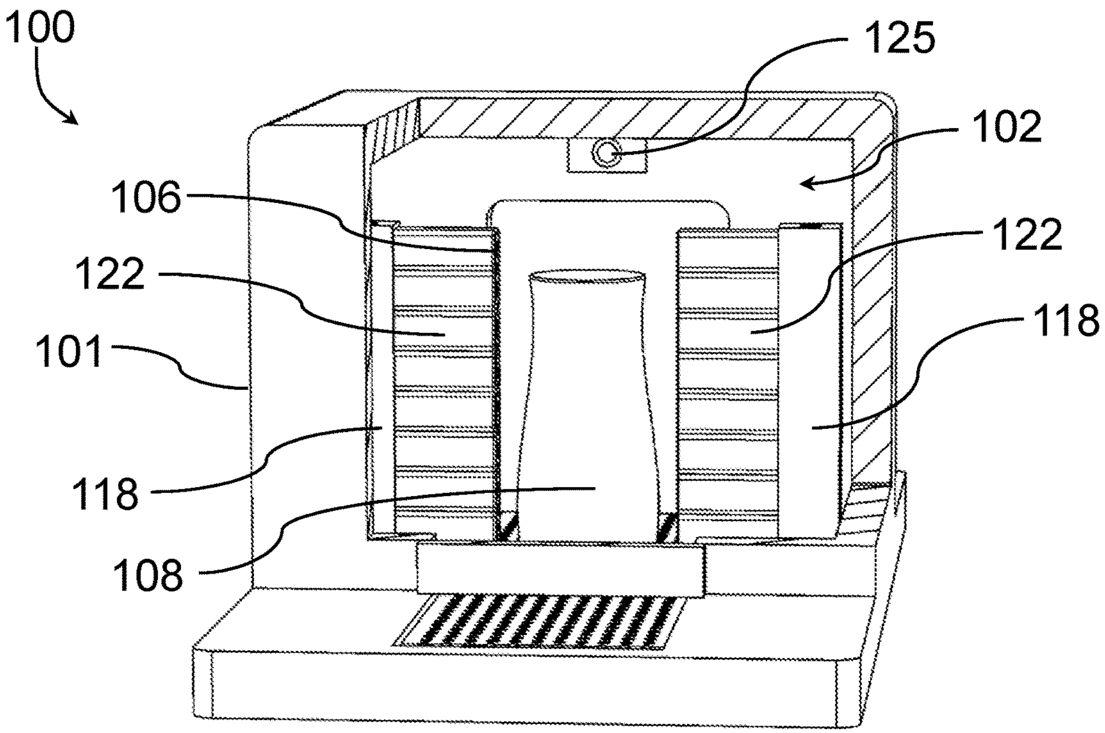
FIGS. 6A and 6B are isometric cut-away views of a housing of the reusable food or beverage container sanitizing and washing system with conveyance containing a UV light source, a washing nozzle, and a profiler having multiple linear moving members in accordance with embodiments of the present invention.
Figure 6B:
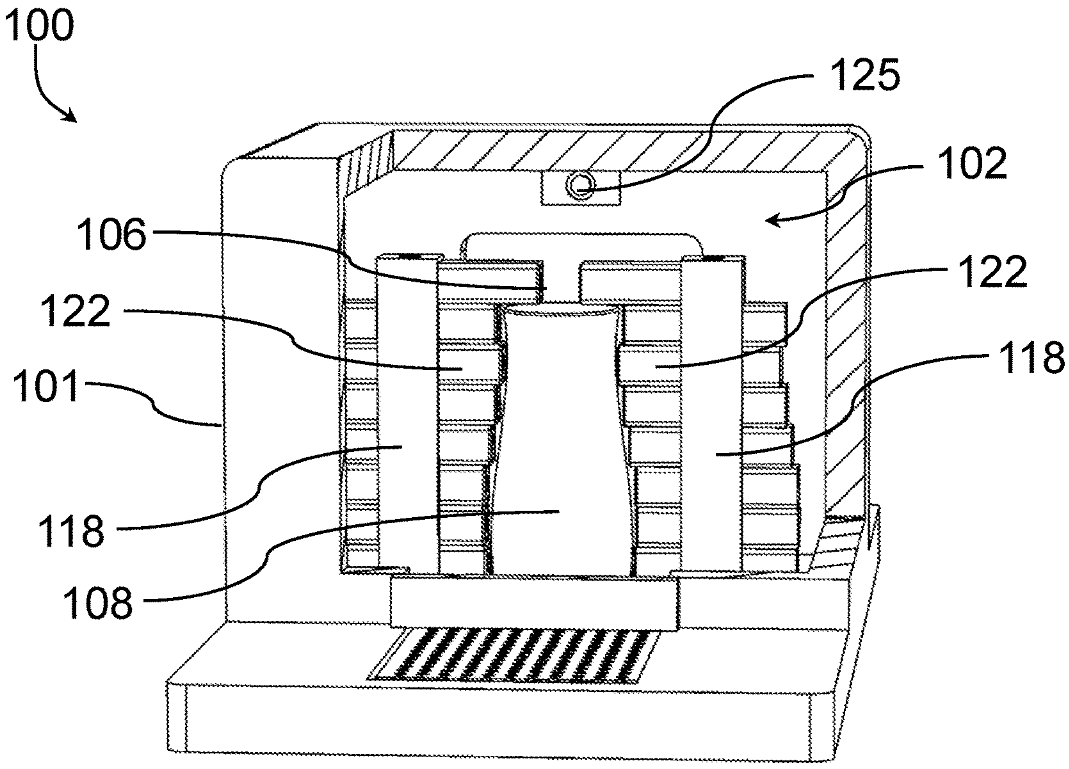
Figure 7:
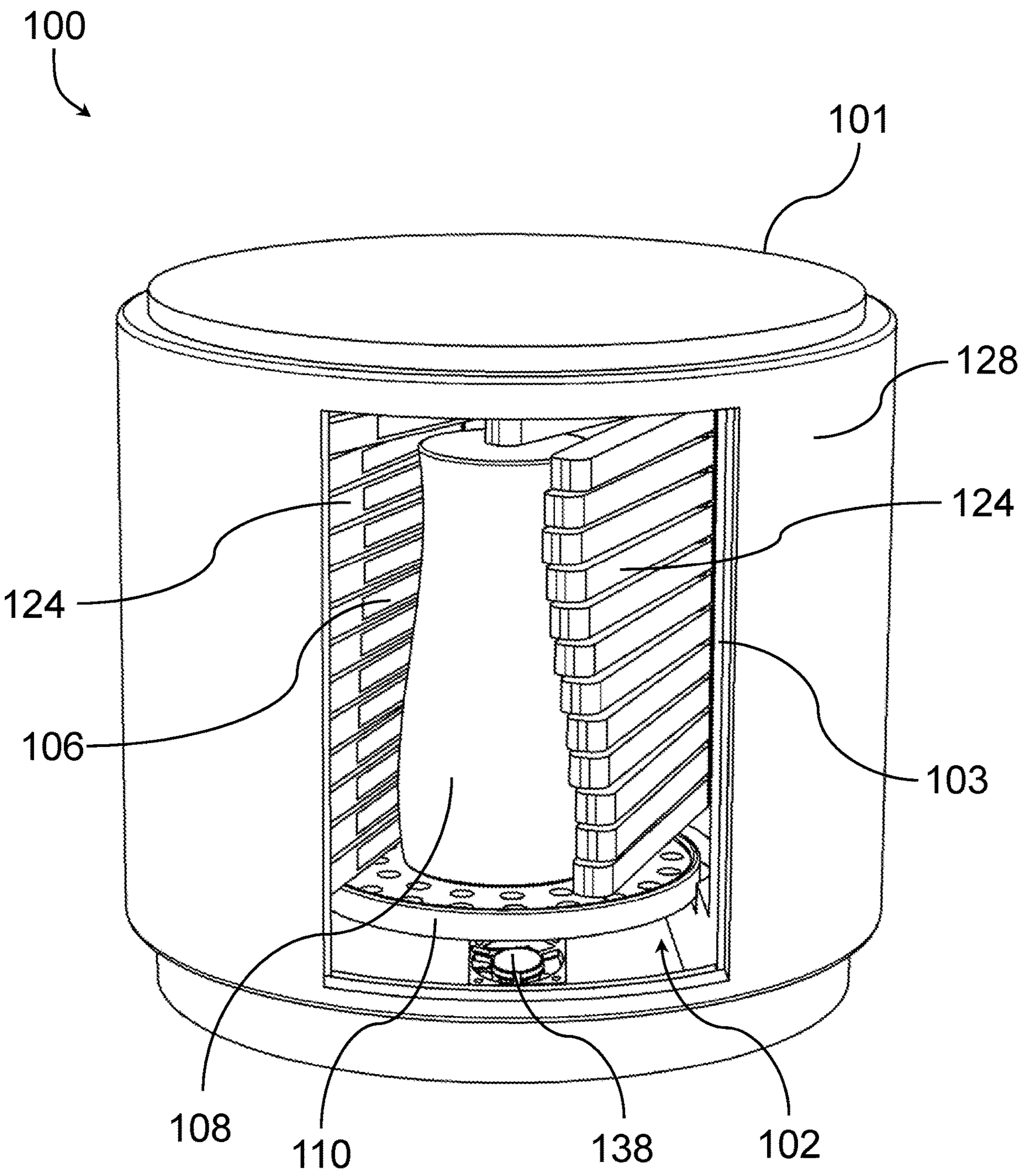
FIG. 7 is an isometric view of a revolving housing of the reusable food or beverage container sanitizing and washing system containing a UV light source, a washing nozzle, a dryer, and a profiler having multiple articulating members in accordance with embodiments of the present invention.

In accordance with example embodiments, the UV light source(s) 106 of the profiler 118 are mounted to multiple movable profiling members which can more accurately adjust to a variety of container profiles, such as the linear motion profiling members 122 shown in FIGS. 6A-6B and the pivoting profiling members 124 shown in FIG. 7. The positioning of the profiling members 120, 122, 124 of the profiler 118 close to the surface of the food or beverage container 108 can be achieved using one or more sensors such as a vision system 125, proximity sensors, or stall sensors incorporated into the profiler 118 used to detect when the profiling arms contact the surface, then back off slightly. In all embodiments, either the food or beverage container 108 or UV light source(s) 106 can be rotated, for example with a rotating draining base 110 as shown in FIG. 7, to ensure all surfaces are evenly sanitized and washed without requiring additional time or an excessive number of UV light sources 106 or washing nozzles 116. In some embodiments, the profiling members 120, 122, 124 of the profiler 118 can be used to hold the food or beverage container in position in place of or in addition to the use of a stabilizer 136 (refer to FIG. 4) as previously described.

Alternately, in certain embodiments where a standardized food or beverage container 108 is used, the profiler 118 (including members 120, 122, 124) or the chamber 102 itself can have a fixed shape or configuration that conforms to the dimensions of the standardized container 108, such that the one or more UV light sources 106 are in close proximity to the surface(s) of the standardized food or beverage container 108. This would simplify the system 100 as the profiler 118 would not require one or more sensors such as a vision system 125, proximity sensors, or stall sensors incorporated into the profiler 118 used to detect when the profiling arms contact the surface, then back off slightly.

In other embodiments, where the food or beverage container 108 is provided with an identification device, such as a radio frequency identification (RFID) tag, bar-code, QR code, or the like, the identification device can be used to identify the food or beverage container 108 including the type or shape of the container 108 such that the profiler 118, stabilizer 136, washing nozzle 116, and centering arms 114 can adjust to conform to the shape of the identified food or beverage container 108. In still other embodiments, the intensity, duration, or a combination of both of the sanitization and washing cycle can be adjusted to an optimized setting for the identified food or beverage container 108.

Figure 8:
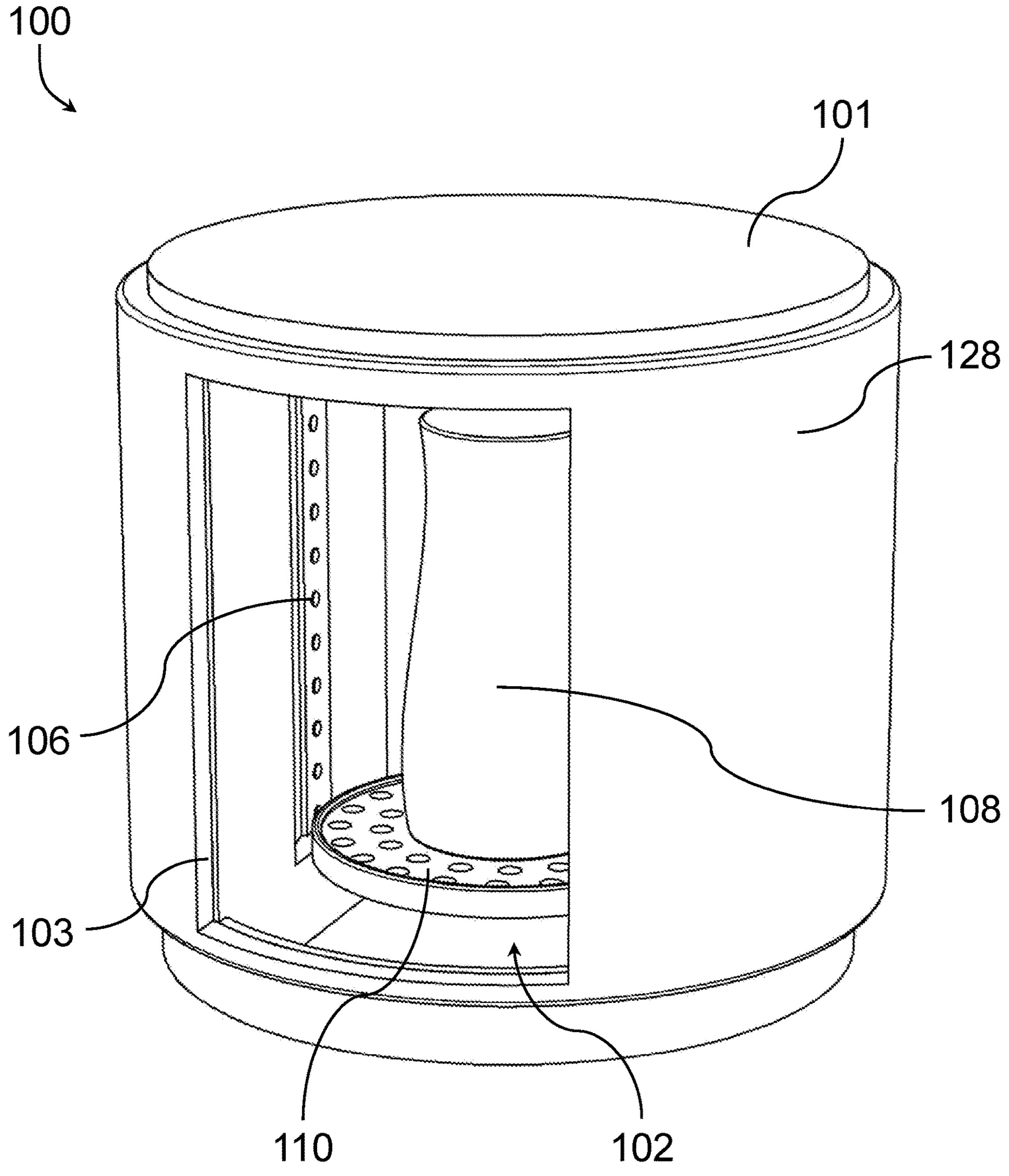
FIG. 8 is an isometric view of a revolving housing of the reusable food or beverage container sanitizing and washing system containing a fixed position UV light source, in accordance with embodiments of the present invention.

In accordance with example embodiments of the system 100, such as seen in FIG. 7 and FIG. 8, the housing 101 or one or more sliding members 128 of the housing 101 providing the access door 103 can be rotated or revolved around the chamber 102 to move the access door 103 between an open state providing access to the chamber 102 or a closed state blocking access to the chamber 102.

In example embodiments, where a minimum and maximum diameter of a food or beverage container 108 fall within a known range, the UV light source 106, is located in a fixed position on an interior side wall of the chamber 102, as shown in FIG. 8. The known intensity of the UV light source 106 and rotational speed of the rotating draining base 110 ensure a minimum desired UV dose for the exterior surfaces of the food or beverage container 108 within the minimum and maximum diameter range. Although the intensity of the UV radiation on the minimum diameter surfaces of food or beverage containers 108 is less than that on the maximum diameter surfaces, the shorter circumference when rotating at the same speed, i.e., revolutions per minute, past the UV light source 106 means that the smaller diameter surfaces of food or beverage container 108 are exposed for a longer duration than the larger diameter surfaces food or beverage container 108. Since the dose received is the product of intensity and exposure time as previously described, the resultant dose received on the minimum diameter surfaces of a food or beverage container 108 that is further from the UV light source 108 is close to, and can even be greater than, the dose received on a maximum diameter surfaces of a food or beverage container 108.

In the same manner that the diameter of the food or beverage container determines the exposure time to the UV light source 106 when rotating on the rotation draining base 110 as previously described for FIG. 8, when a food or beverage container 108 is placed off-center on the rotating draining base, the surfaces located farther away from the center of the rotating draining base 110 are exposed to higher intensity UV radiation but for a shorter duration than the surfaces located closer to the center of the rotating draining base 110, keeping the dose received on all surfaces relatively close, such as within a difference of 25%. When such a dose differential is acceptable, the use of a centering device, such as pivoting centering arms 114 as previously described, is not required.

Figure 9A:
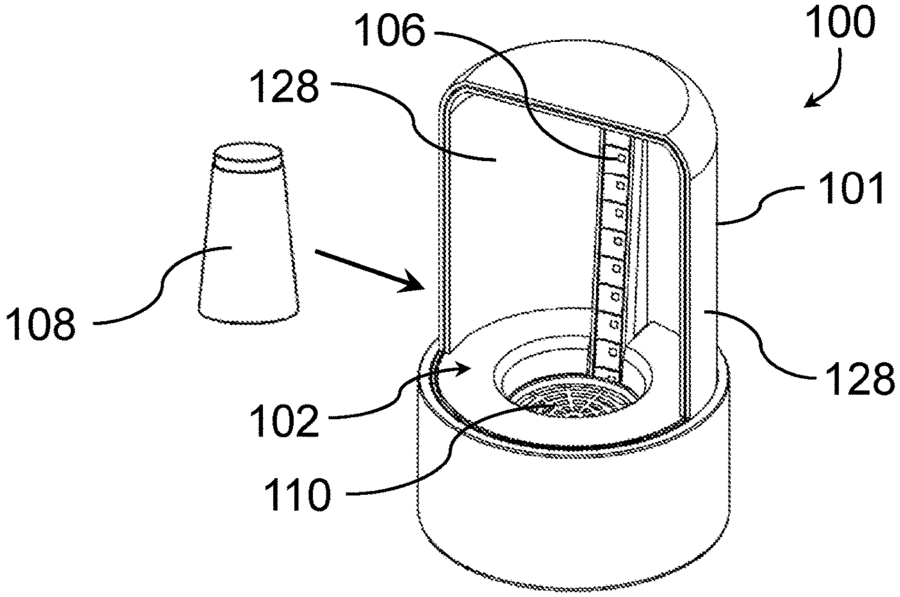
FIGS. 9A, 9B, 9C are isometric views of a housing of the reusable food or beverage container sanitizing and washing system containing nesting sliding members in accordance with embodiments of the present invention.
Figure 9B:
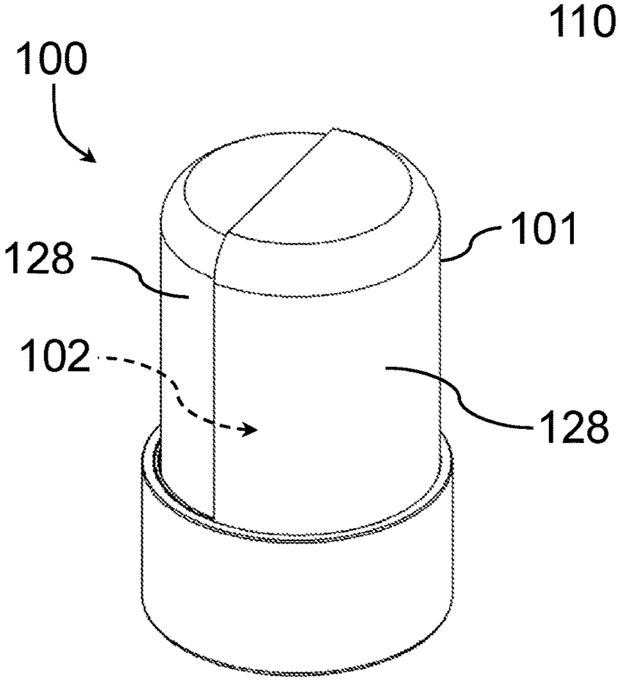
Figure 9C:
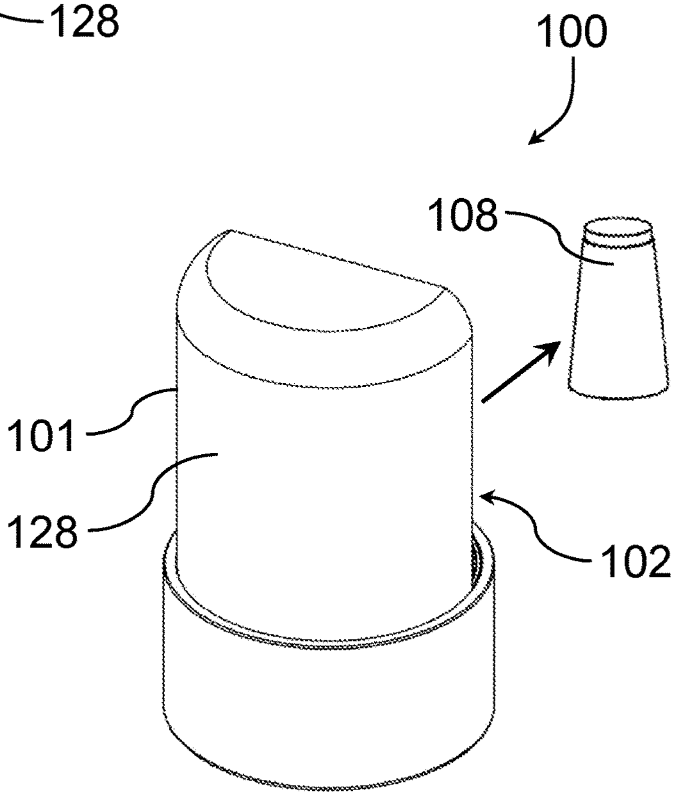

In accordance with an embodiment of the system 100 as shown in FIGS. 9A-9C, the housing 101 is comprised of 2 or more nesting sliding members 128 which rotate from having an opening on the entry ("dirty") side (FIG. 9A) to a closed position for the sanitization and washing cycle (FIG. 9B) to having an opening on the exit ("clean") side of the system (FIG. 9C). Each sliding member 128 can include portions of both the sides and top of the housing 101, such that when nested in an open position, provide a large and easily accessible opening for placing a food or beverage container 108 into the chamber 102 (FIG. 9A) and removing a food or beverage container 108 from the chamber 102 (FIG. 9C), as well as provide a fully enclosed chamber 102 when rotated to a closed position (FIG. 9B). In an embodiment, in order to keep access to the opening as unobstructed as possible, the UV light source 106 is located on the inner surface of the innermost nesting sliding member 128 as shown in FIG. 9A.

As only the interior surfaces of the food or beverage container 108 get wet during the sanitization and washing cycle, it is generally not required to dry those surfaces prior to handling or use in order to minimize the duration of the sanitization and washing cycle and overall energy usage of the system. In some embodiments when drying or partial drying is desired, the use of one or more dryers 138 to provide heat or moving air or combination of both can be used as shown in FIG. 7. The air moving across the surfaces of the food or beverage container 108 can be intended to dry via evaporation or to physically push the cleaning fluid off the surface using a jetting process, or a combination of each. Other known drying processes, such as but not limited to absorption, surface wiping, vacuum to remove cleaning fluid, heating, and the like are also practicable. In accordance with embodiments of the system 100, the rotating draining base 110 or conveyor 112 (refer to FIG. 3A) can themselves be utilized to use motion to generate the force to remove cleaning fluid from the food or beverage containers 108, such as by rapid acceleration or deceleration, centrifugal force, spinning, shaking, or the like. Any combination of the use of moving air, heat, physical removal, and physical movement of the food or beverage containers 108 to decrease drying time is also practicable.

Figure 10A:
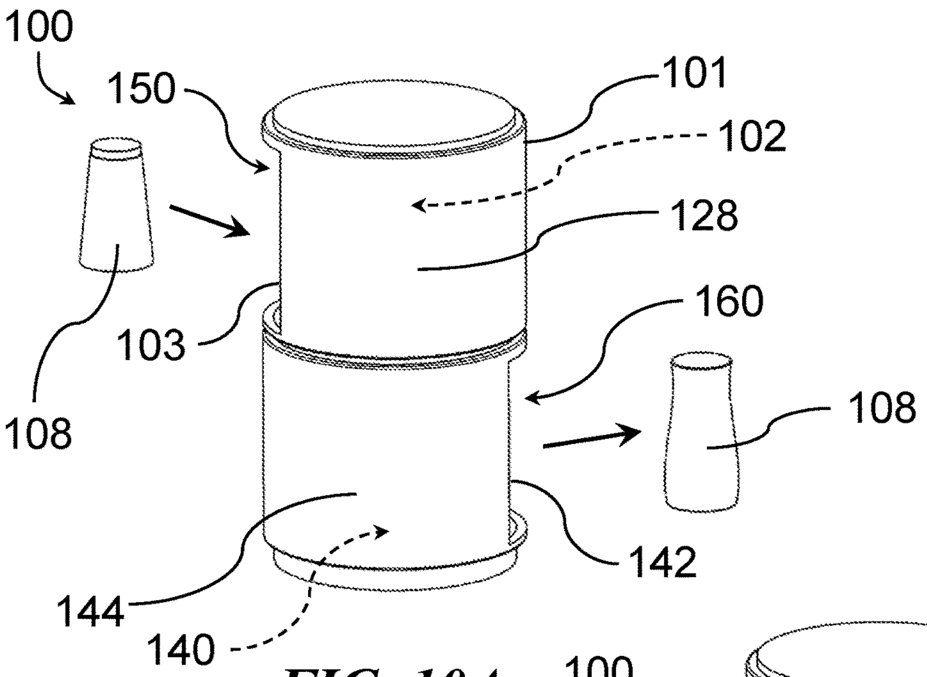
FIGS. 10A, 10B, 10C are isometric views of a housing of the reusable food or beverage container sanitizing and washing system containing two chambers for sanitizing and washing in accordance with embodiments of the present invention.
Figure 10B:
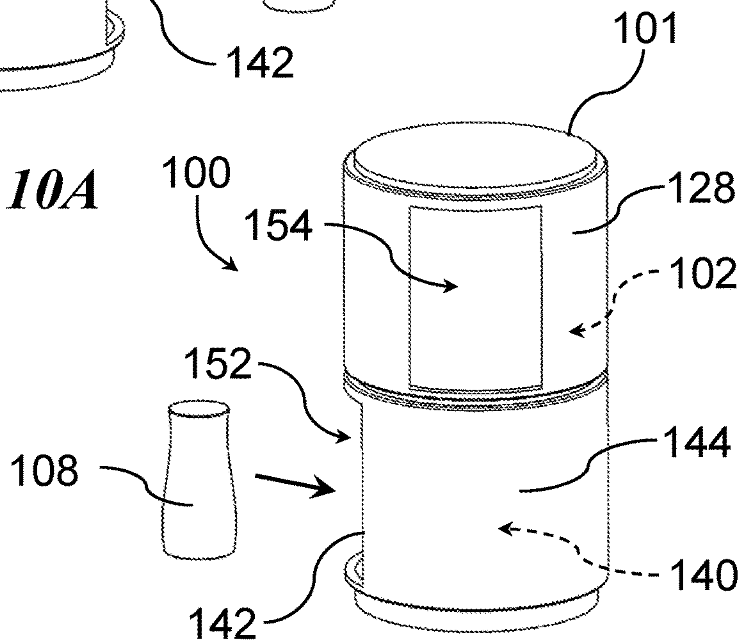
Figure 10C:
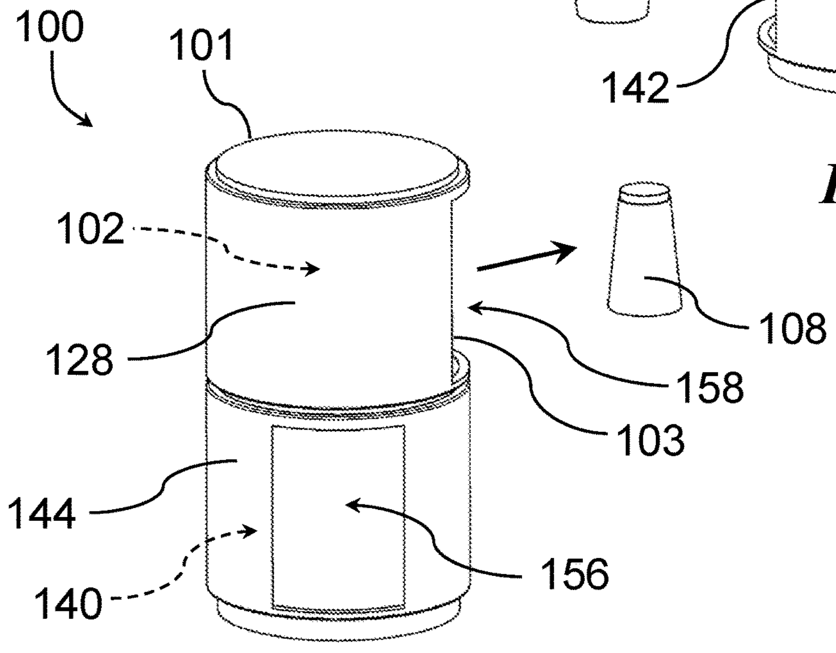

For retail locations where customers frequently make use of reusable food or beverage containers 108, the time required to achieve the appropriate level of sanitization and washing may be too long when high through-put, or no waiting time to load, is desired. FIGS. 10A-10C show a dual stacked version of the revolving door system from FIG. 7. Here a second chamber 140 is provided that is sized, dimensioned, and configured to envelope a food or beverage container 108. A second access door 142 is provided on second sliding member 144. The second access door 142 provides access to the second chamber 140 when the second access door 142 is in an open state and blocks access to the second chamber 140 when the second access door 142 is in a closed state. At least one UV light source 106 (not shown in this figure) is disposed within the second chamber 140 and configured to direct UV light at a predetermined intensity level and time duration onto the exterior surfaces of a food or beverage container 108 positioned inside the second chamber 140 in such a way as to result in sanitizing of the exterior surfaces of the food or beverage container 108. At least one washing nozzle 116 (not shown in this figure) is disposed within the second chamber 140 and configured to spray cleaning fluid onto the interior surfaces of a food or beverage container 108 positioned inside the second chamber 140 in such a way as to result in washing of the interior surfaces of the food or beverage container 108. The housing 101, in this case, the first sliding member 128 and second sliding member 144 of the housing 101, rotate to expose the "dirty" side opening, the "clean" side opening, or a closed position with no openings for the sanitization and washing process to take place within the chambers 102, 140. In FIG. 10A the first sliding member 128 of the housing 101 is in a first position 150 where the first access door 103 is in an open state for receiving an unsanitized and unwashed food or beverage container 108. The second sliding member 144 is in a second position 160 where the second access door 142 is in an open state allowing for the removal of a sanitized and washed food or beverage container 108 from the second chamber 140. In FIG. 10B the first sliding member 128 is moved such that the first access door 103 is in a closed state 154 during which a sanitization and washing cycle is run. The second sliding member 144 is moved to a first position 152 where the second access door 142 is in an open state for receiving an unsanitized and unwashed food or beverage container 108. In FIG. 10C the first sliding member 128 is moved to a second position 158 where the first access door 103 is in an open state allowing for the removal of the now sanitized and washed food or beverage container 108. The second sliding member 144 has been moved such that the second access door 142 is in a closed state 156 during which a sanitization and washing cycle is run in the second chamber 140. The sliding members 128, 144 can then be moved back to the positions shown in FIG. 10A.

By having dual systems, such as the stacked systems as shown in FIGS. 10A-10C, or some other combination of two or more systems, the overall through-put of the system 100 is increased and wait times to use the system are decreased as one system can be loaded or unloaded while the other is running the sanitization and washing process. These systems can be individual stand-alone systems, or a single system containing multiple chambers.

Figure 11:
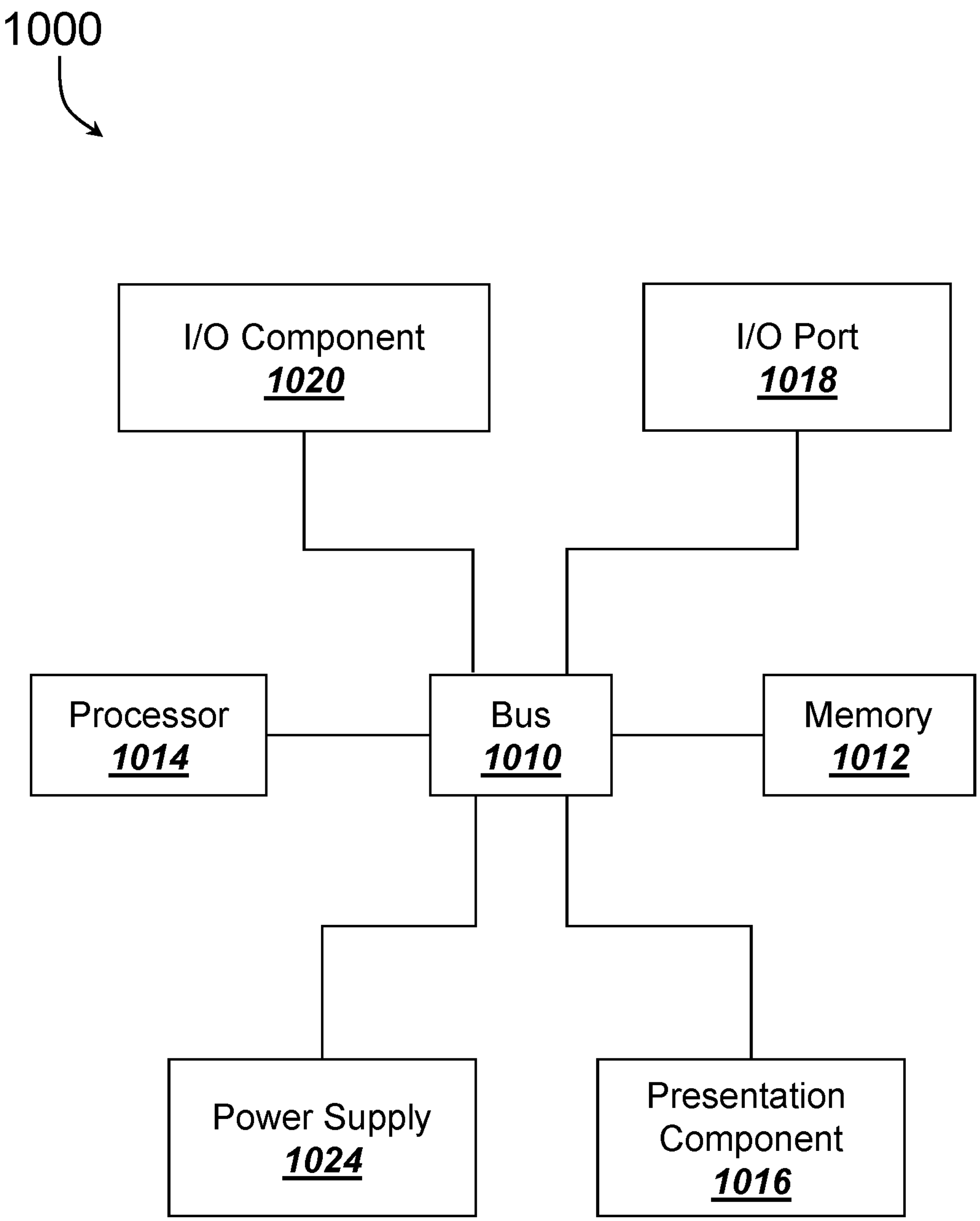
FIG. 11 is a diagrammatic illustration of a computing device and related hardware for use in implementation of the present invention.

FIG. 11 depicts an example electronic, computer, or computing device 1000 that can be used to implement one or more aspects of the present invention. The functionality and hardware of such computing device 1000 may be implemented in any of the electronic hardware systems or subsystems described herein as involving or using a "computer" or "computing device" or the like, or related hardware for providing all or part of the described functionality, provided as a separate device or integrated into a system or subsystem described herein, as would be appreciated and understood by those of skill in the art. The terms "computer", "computing device", and the like utilized herein are intended to mean a processor at its most basic form, on up to more complex computing systems, including servers and cloud-based systems, in accordance with conventional meanings of such terms. However, for purpose of completeness, example components and related accessories that are intended to be encompassed by the use of the terms "computer", "computing device", "processor", and the like will be provided below in example nonlimiting form.

The computing device 1000 is merely an illustrative example of a suitable computing environment and in no way limits the scope of the present invention. An "electronic device", "remote device," or "personal electronic device" as represented in figures and description herein, can include a "workstation," a "server," a "laptop," a "desktop," a "hand-held device," a "mobile device," a "tablet computer," a "processor," or other computing devices, as would be understood by those of skill in the art. Given that the computing device 1000 is depicted for illustrative purposes, embodiments of the present invention may utilize any number of computing devices 1000 in any number of different ways to implement a single embodiment of the present invention. Accordingly, embodiments of the present invention are not limited to a single computing device 1000, as would be appreciated by one with skill in the art, nor are they limited to a single type of implementation or configuration of the example computing device 1000.

The computing device 1000 can include a bus 1010 that can be coupled to one or more of the following illustrative components, directly or indirectly: a memory 1012, one or more processors 1014, one or more presentation components 1016, input/output ports 1018, input/output components 1020, and a power supply 1024. One of skill in the art will appreciate that the bus 1010 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, the figures herein are merely illustrative of an exemplary computing device 1000 that can be used to implement one or more embodiments of the present invention, and in no way limits the invention.

The computing device 1000 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 1000.

The memory 1012 can include computer-storage media in the form of volatile and/or nonvolatile memory. The memory 1012 may be removable, non-removable, or any combination thereof. Exemplary hardware devices are devices such as hard drives, solid-state memory, optical-disc drives, and the like. The computing device 1000 can include one or more processors that read data from components such as the memory 1012, the various I/O components 1020, etc. Presentation component(s) 1016 present data indications to a user or other device. Exemplary presentation components include a display device, speaker, printing component, vibrating component, etc.

The I/O ports 1018 can enable the computing or electronic device 1000 to be logically coupled to other devices, such as I/O components 1020. Some of the I/O components 1020 can be built into the computing device 1000. Examples of such I/O components 1020 include a sensor (including but not limited to: weight sensor, infrared sensor, camera, chemical sensor, microphone, or the like), keypad, touchpad, joystick, recording or storage device, game pad, satellite dish, scanner, printer, wireless device, networking device, and the like, as appropriate.

To any extent utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about" and "approximately" are intended to cover variations that may existing in the upper and lower limits of the ranges of subjective or objective values, such as variations in properties, parameters, sizes, and dimensions. In one non-limiting example, the terms "about" and "approximately" mean at, or plus 10 percent or less, or minus 10 percent or less. In one non-limiting example, the terms "about" and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A reusable food or beverage container sanitizing and washing system, comprising:

a housing;

a chamber inside the housing that is sized, dimensioned, and configured to envelope a reusable food or beverage container;

an access door providing access to the chamber when the access door is in an open state and blocking access to the chamber when the access door is in a closed state;

at least one UV light source disposed within the chamber and configured to direct UV light at a predetermined intensity level and time duration onto a reusable food or beverage container positioned inside the chamber in such a way as to result in sanitizing of exterior surfaces of the reusable food or beverage container; and at least one washing nozzle configured to extend into an interior of the reusable food or beverage container to spray cleaning fluid to wash only interior surfaces of the reusable food or beverage container;

wherein when the access door is in the closed state a sanitization and washing cycle is initiated using the at least one UV light source and the at least one washing nozzle and when the sanitization and washing cycle is complete, the access door is moved to an open state.

2. The sanitizing and washing system of claim 1, further comprising a retrieval door disposed on a different side of the chamber than the access door, the retrieval door providing access to the chamber when the retrieval door is in an open state and blocking access to the chamber when the retrieval door is in a closed state.

3. The sanitizing and washing system of claim 2, wherein the access door is configured to receive an unsanitized and unwashed reusable food or beverage container and the retrieval door is configured to allow retrieval of a sanitized and washed reusable food or beverage container after the sanitization and washing cycle.

4. The sanitizing and washing system of claim 3, further including a conveyor configured to receive an unsanitized and unwashed reusable food or beverage container, move the unsanitized and unwashed reusable food or beverage container into the chamber through the access door, and move a sanitized and washed reusable food or beverage container out of the chamber through the retrieval door.

5. The sanitizing and washing system of claim 1, further comprising a container centering device disposed within the chamber.

6. The sanitizing and washing system of claim 1, wherein the at least one UV light source comprises an array of UV lights disposed on an interior surface of one or more sides of the chamber.

7. The sanitizing and washing system of claim 1, wherein the predetermined intensity level and time duration result in a UV dose of at least 4 mJ/cm2.

8. The sanitizing and washing system of claim 1, wherein the predetermined intensity level and time duration result in a UV dose of about 8 mJ/cm2.

9. The sanitizing and washing system of claim 1, wherein the predetermined intensity level and time duration result in a UV dose of at most 24 mJ/cm2.

10. The sanitizing and washing system of claim 1, wherein the predetermined intensity level and time duration result in a UV dose of between about 4 mJ/cm2 and 8 mJ/cm2.

11. The sanitizing and washing system of claim 1, wherein the predetermined intensity level and time duration result in a UV dose of between about 4 mJ/cm2 and 24 mJ/cm2.

12. The sanitizing and washing system of claim 1, wherein the at least one UV light source is disposed on a container profiler that is configured to conform to a shape of the reusable food or beverage container to place the at least one UV light source in proximity to an exterior surface of the reusable food or beverage container allowing for effective sanitation at a lower intensity level or time duration relative to having the at least one UV light source distal to the exterior surface of the reusable food or beverage container.

13. The sanitizing and washing system of claim 12, wherein the profiler comprises one or more members having at least one UV light source mounted thereon, the members configured to move toward an exterior surface of the reusable food or beverage container to place the UV light in proximity to the exterior surface of the reusable food or beverage container.

14. The sanitizing and washing system of claim 12, wherein the container profiler comprises one or more sensors for detecting a shape of the reusable food or beverage container.

15. The sanitizing and washing system of claim 12, wherein the container profiler is configured to rotate around the reusable food or beverage container to distribute application of UV light.

16. The sanitizing and washing system of claim 1, wherein the at least one washing nozzle is disposed and configured to extend into the interior of the reusable food or beverage container when activated to wash only the interior surfaces of the reusable food or beverage container.

17. The sanitizing and washing system of claim 1, further comprising a draining base configured to rotate for rotating the reusable food or beverage container within the chamber to dry the interior surfaces of the reusable food or beverage container after the washing cycle.

18. The sanitizing and washing system of claim 1, further comprising a flipping device configured to receive a reusable food or beverage container in a substantially upright position and turn the container over to allow the container to drain during or after the washing cycle.

19. The sanitizing and washing system of claim 1, further comprising one or more dryers adapted to dry the interior surfaces of the reusable food or beverage container at an end of the washing cycle.

20. The sanitizing and washing system of claim 1, wherein the housing rotates around the chamber and wherein the access door connected to the housing receives unsanitized and unwashed reusable food or beverage container in a first position located on a first side of the chamber and rotates to a second position located on second side of the chamber to provide access to a sanitized and washed reusable food or beverage container.

21. The sanitizing and washing system of claim 1, wherein nesting sliding members of the housing rotate around the chamber and wherein the sliding members provide an access door that receives unsanitized and unwashed reusable food or beverage container in a first position located on a first side of the chamber and rotate to a second position located on second side of the chamber to provide access to a sanitized and washed reusable food or beverage container.

22. The sanitizing and washing system of claim 21, wherein the at least one UV light source is disposed on an inner surface of an innermost nesting sliding member.

23. The sanitizing and washing system of claim 1, further comprising:

a second chamber inside the housing that is sized, dimensioned, and configured to envelope the reusable food or beverage container;

a second access door providing access to the second chamber when the second access door is in an open state, and blocking access to the second chamber when the second access door is in a closed state;

at least one UV light source disposed within the second chamber and configured to direct UV light at a predetermined intensity level and time duration onto the reusable food or beverage container positioned inside the second chamber in such a way as to result in sanitizing of surfaces of the reusable food or beverage container; and at least one washing nozzle disposed within the second chamber and adapted to extend into an interior of the reusable food or beverage container to spray cleaning fluid to wash only the interior surfaces of the reusable food or beverage container;

wherein when the second access door is in the closed state the sanitization and washing cycle is initiated using the at least one UV light source and the at least one washing nozzle disposed in the second chamber and when the sanitization and washing cycle is complete, the second access door is moved to the open state.

24. A method for sanitizing and washing a reusable food or beverage container, the method comprising:

providing a reusable food or beverage container sanitizing and washing system, comprising:

a housing;

a chamber inside the housing that is sized, dimensioned, and configured to envelope a reusable food or beverage container;

an access door providing access to the chamber when the access door is in an open state and blocking access to the chamber when the access door is in a closed state;

at least one UV light source disposed within the chamber and configured to direct UV light at a predetermined intensity level and time duration onto a food or beverage container positioned inside the chamber in such a way as to result in sanitizing of surfaces of the food or beverage container;

at least one washing nozzle disposed within the second chamber and adapted to extend into an interior of the reusable food or beverage container to spray cleaning fluid to wash only interior surfaces of the reusable food or beverage container;

wherein when the access door is in the closed state a sanitization and washing cycle is initiated using the at least one UV light source and the at least one washing nozzle disposed in the second chamber and when the sanitization and washing cycle is complete, the access door is moved to the open state;

inserting an unsanitized and unwashed reusable food or beverage container into the chamber;

initiating a sanitization and washing cycle sanitizing and washing the reusable food or beverage container; and retrieving a now sanitized and washed reusable food or beverage container from the chamber.

* * * * *